(12) United States Patent
Caseres et al.

(10) Patent No.: US 9,689,802 B2
(45) Date of Patent: Jun. 27, 2017

(54) SYSTEMS, METHODS AND APPARATUS FOR ANALYSIS OF MULTIPHASE FLUID MIXTURE IN PIPELINES

(75) Inventors: Leonardo J. Caseres, Helotes, TX (US); James F. Dante, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 195 days.

(21) Appl. No.: 13/537,728

(22) Filed: Jun. 29, 2012

(65) Prior Publication Data
US 2014/0004619 A1    Jan. 2, 2014

(51) Int. Cl.
| | |
|---|---|
| G01N 21/00 | (2006.01) |
| G01N 21/80 | (2006.01) |
| G01N 21/3554 | (2014.01) |

(52) U.S. Cl.
CPC ......... *G01N 21/80* (2013.01); *G01N 21/3554* (2013.01)

(58) Field of Classification Search
None
See application file for complete search history.

(56) References Cited

U.S. PATENT DOCUMENTS

| | | | | |
|---|---|---|---|---|
| 5,853,669 | A | * | 12/1998 | Wolfbeis ............ G01N 31/221 422/408 |
| 7,841,249 | B2 | | 11/2010 | Tormoen |
| 2005/0145018 | A1 | | 7/2005 | Sabata et al. |
| 2006/0247869 | A1 | | 11/2006 | Lucero |
| 2008/0041173 | A1 | | 2/2008 | Tormoen |
| 2010/0145634 | A1 | | 6/2010 | Pinguet et al. |
| 2011/0098938 | A1 | | 4/2011 | Huang et al. |

OTHER PUBLICATIONS

Kalinina, et al; "Portable Optical Water-and-Oil Analyzer Based on a Mid-IR (1.6-2.4 um) Optron Consisting of an LED Array and a Wideband Photodiode", Technical Physics, vol. 55, No. 2, pp. 258-263 (2010).
Nesic, et al; "A New Updated Model of CO2/H2S Corrosion in Multiphase Flow"; Paper 08535, NACE Corrosion 2008, Conference & Expo Atlanta, GA (2008).
Raghuraman, et al; "Real-Time Downhole pH Measurement Using Optical Spectroscopy", SPE Reservoir Evaluation & Engineering, 10 (3): 302-311, SPE-93057-PA (2007).
Shi, et al; "Optical pH Sensor With Rapid Response Based on a Fluorescein-Intercalated Layered Double Hydroxide", Advanced Functional Materials, 20, pp. 3856-3863 (2010).
Zhang, et al; "Corrosion-Sensing Behavior of an Acrylic-Based Coating System"; CORROSION—Corrosion Science Section, vol. 55, No. 10, pp. 957-967 (1999).

* cited by examiner

*Primary Examiner* — Robert Xu
(74) *Attorney, Agent, or Firm* — Grossman, Tucker et al

(57) ABSTRACT

An apparatus and method to measure water content and water pH of multiphase fluid mixtures of water and oil. The apparatus employs a water content sensor containing an infrared light source and a photodetector. The pH sensor includes a pH indicator that exhibits a color change in an oleophobic coating including an image recording device. The apparatus and method may be applied to measure water fraction and pH within oil/water pipelines.

13 Claims, 12 Drawing Sheets

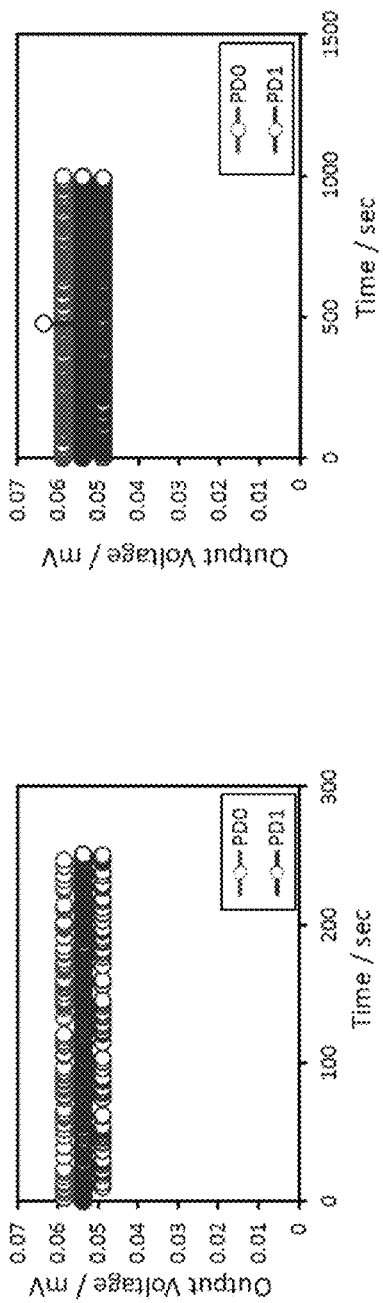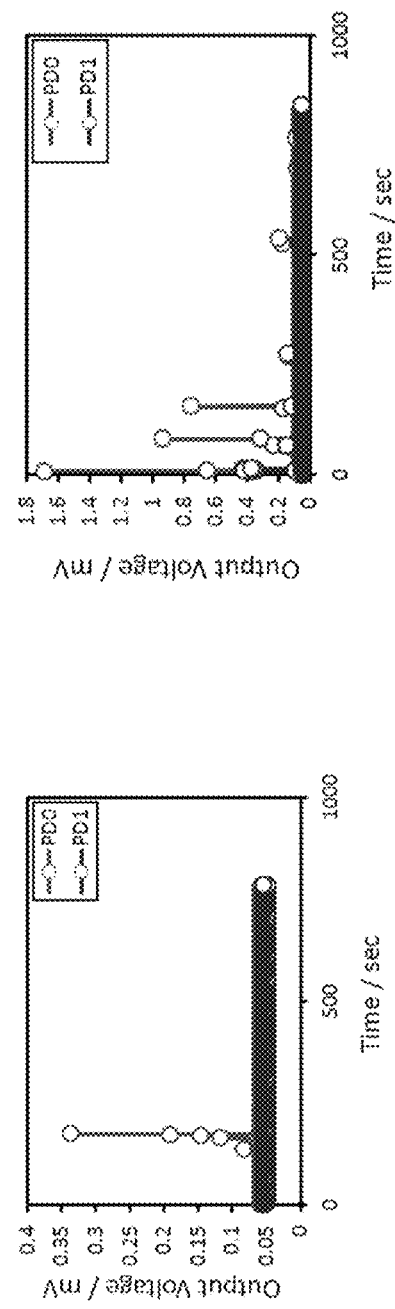
FIG. 9A
FIG. 9B
FIG. 9C
FIG. 9D

SYSTEMS, METHODS AND APPARATUS FOR ANALYSIS OF MULTIPHASE FLUID MIXTURE IN PIPELINES

FIELD

The present invention relates to systems, methods and apparatus for analysis of a multiphase fluid mixture of water and crude oil for water content and pH level of the water phase.

BACKGROUND

Determination of free water content, which may also be referred to as water fraction or water percentage, in a multiphase fluid mixture of water and crude oil is of great practical interest to the oil and gas industry, particularly from a point of view of corrosion monitoring and mitigation of the many pipelines which contain and serve to transport the flowing multiphase mixture.

The presence of free water in crude oil during transportation in offshore and onshore pipelines has been associated with accelerated corrosion rates in oil and gas production operations, particularly in the pipelines as well as associated equipment (e.g. valves) which make contact with the flowing mixture. Today, portable apparatus which offer rapid analysis of free water content in crude oil, particularly in deep-sea environments, are lacking.

Methods of analysis may include gravitational settling, centrifugation, thermal and cold treatments, microwave separation, ultrasonic separation, and separation under the action of an electric field (Samigullin and Khaziev, 2005). However, these methods may be considered labor intensive, time-consuming and require bulky equipment. As such, it is generally cumbersome to apply these methods in the field. As a result, there is a need for an apparatus to simply detect and measure free water content in a water and oil multiphase mixture, for both offshore and onshore applications.

In addition to detection and measurement of free water content in crude oil, it is of critical importance to determine the properties of the free water in the multiphase mixture, such as its pH (potential Hydrogen). Accurate pH measurement of the water phase allows for more accurate selection of appropriate completion materials and effective planning for scale formation treatment and inhibition. Numerous corrosion predictive models are being developed to accurately predict corrosivity as a function of pH and other parameters of multiphase environments and define accurate limits of use of carbon steel pipes (Nesic et al., 2008). However, many of these models are overly conservative or focus only on a narrow range of parametric effects, thereby limiting their scope of applicability. Furthermore, for these models, pH is calculated from the $CO_2/H_2S$ solution equilibrium.

There is a need to measure and validate the pH of free water phase in a crude oil and water multi-phase mixture in the field by using an apparatus which may measure such pH of free water in pipelines in-situ. A team led by Raghuraman (2007) developed a sensor that measures the pH of formation water at reservoir conditions in situ. Formation water may be understood as the water that is initially obtained during the oil extraction process. The sensor uses pH-sensitive dyes that change color according to the pH of the formation water. However, this sensor requires the implementation of several components typical of downhole optical fluid analyzers.

SUMMARY

This disclosure provides systems, methods and apparatus for analysis of a water and oil multiphase fluid mixture in a pipeline, particularly for water content and its pH level in the multiphase fluid mixture. The systems, methods and apparatus may particularly make use of sensors, such as a water sensor comprising a light source, such as an infrared (IR) light emitting diode (LED), and a photodetector capable of converting light into either electric current or voltage, such as a photodiode (PD); and a pH sensor comprising a color camera, such as a complementary metal-oxide-semiconductor (CMOS) color camera, and a pH sensitive indicator that includes a coating that imparts oleophobicity (repellency to oil).

The systems, methods and apparatus are particularly applicable to onshore and offshore liquid pipelines, particularly containing a water and oil multiphase liquid mixture. The apparatus may particularly be used as a mobile sensor that is capable of traveling with a flow of the multiphase mixture along the pipeline to monitor free water content and its pH over the entire length of the pipeline in a single run.

In terms of operation, a water content sensor may be provided by an IR light source and the photodetector. The light source and the photodetector may be arranged such that light from the IR light source may be transmitted through the multiphase mixture and detected by the photodetector. The IR light source may more particularly comprise a plurality of light emitting diodes and the photodetector may more particularly comprise a plurality of photodiodes. The IR light emitting diodes and photodiodes may be located on opposing sides of a fluid flow passage of the apparatus through which the multiphase mixture may be allowed to flow. The IR photodiodes may be configured to provide an output voltage which changes based on the water content in the multiphase mixture, and may be able to detect the water content in a range of 0% to 100%, and in increments of 1 percent or less.

For example, when the multiphase mixture may be nearest 100% oil, it may be understood that the lowest relative amount of light from the IR light source may pass through the multiphase mixture to the photodiodes. In response to a relatively low amount of light being detected by the photodetector, the output voltage of the photodetector (photodiodes) may be near zero. On the other hand, when the multiphase mixture would be nearest 100% water, it may be understood that the highest relative amount of light from the IR light source may pass through the multiphase mixture to the photodetector. In this situation, the output voltage of the photodetector (photodiodes) may be at a maximum. Thereafter, from the two output voltages at nearest 100% oil and nearest 100% water, linear interpolation may be used to correlate output voltage of the photodetector (photodiodes) to free water content of the multiphase mixture.

With regards to a water pH sensor, an oleophobic coating (as further defined herein) may be mixed with at least one colorimetric pH indicator to provide a dispersion to be applied to a substrate surface of the apparatus. For example, the oleophobic coating may be combined with one or a plurality of colorimetric pH indicating dye particles which may provide visual (optical) color change indicative of the pH of the water. The color camera may be used to optically capture the color change(s) of the pH indicator(s) with still or video images. Once the color images are obtained, the colors of the pH indicator in the images may be compared to a predetermined scale which correlates indicator color to pH level. From the predetermined scale, the pH level of the water may be determined.

In addition to the oleophobic coating, a protective barrier mesh, such as a polytetrafluoroethylene (PTFE) mesh, may optionally overlie the oleophobic coating containing the pH indicator. This may increase the repellency of the crude oil. In addition to improving separation of the multiphase mixture, the PTFE mesh may also increase the dwell time of the water phase, and reduce the leach rate of the pH indicator from the oleophobic coating.

The sensor apparatus may be equipped with at least one IR LED/photodiode pair for detection and measurement of water content in crude oil. In addition, the use of a color camera, such as a CMOS video camera, arranged to observe changes in the pH-sensitive coating may be included for obtaining pH of the water in a water and oil multiphase fluid mixture. As set forth above, this approach utilizes a coating which undergoes a change in its color when a surrounding oil/water mixture shifts its pH within a specific range. The CMOS camera may be placed adjacent the coating surface to record changes in indicator color for pH determination. In practice, it is contemplated that the sensor apparatus may be sized to fit within a suitable sensor enclosure for travel within the pipeline.

The disclosure herein also provides an apparatus to measure water content and water pH of a multiphase fluid mixture of water and oil, with the apparatus comprising a water content sensor comprising an IR light source and at least one photodetector arranged such that light from the IR light source is passable through the multiphase mixture and detectable by the photodetector, the photodetector arranged to convert the detected light from the light source to an electrical output indicative of the water content of the multiphase fluid mixture. A pH sensor is included comprising a image recording device and a composition including at least one pH indicator with an oleophobic coating that exhibits a color change indicative of a pH level of the water when exposed thereto, the image recording device arranged to record the color change of the pH indicator.

The apparatus may further comprise a flow passage for the multiphase mixture. In certain embodiments, the IR light source and the at least one photodetector may face each other from opposing sides of the flow passage such that light from the light source is detectable by the photodetector.

The flow passage may be at least partially defined by a transparent wall. The light source and the at least one photodetector may be each arranged outside the flow passage behind opposing portions of the transparent wall. The IR light source and the at least one photodetector may also be arranged such that the light from the IR light source is passable through a portion of the transparent wall adjacent the light source to the multiphase mixture and thereafter passable from the multiphase mixture through a portion of the transparent wall adjacent the at least one photodetector.

The image recording device may be arranged outside the flow passage adjacent the transparent wall. The image recording device may also be arranged to record the color change of the pH indicator through the transparent wall. The image recording device may be a camera, such as a video camera. The video camera may be a complementary metal-oxide-semiconductor video camera.

The apparatus may further comprise: (1) a housing configured to roll the apparatus along a pipeline; (2) a data collection device; (3) a power source; (4) a transceiver; and (5) a computer processor and a computer readable storage medium.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein:

FIGS. 9A-9G are graphs of output voltage for the IR LED of the sensor apparatus in FIG. 1 in mixtures of oil/3.5% NaCl solution for a 3.175 mm fluid gap separation between the IR LED and photodiodes (labeled as PD0 and PD1) and a flow rate of 100 mL/min with the following water fractions WF: (A) WF=0, (B) WF=1%, (C) WF=5%, (D) WF=10%, (E) WF=15%, (F) WF=20%, and (G) WF=35%;

FIG. 12A displays the sensor surface prior to exposure.

DETAILED DESCRIPTION

Figure 1:
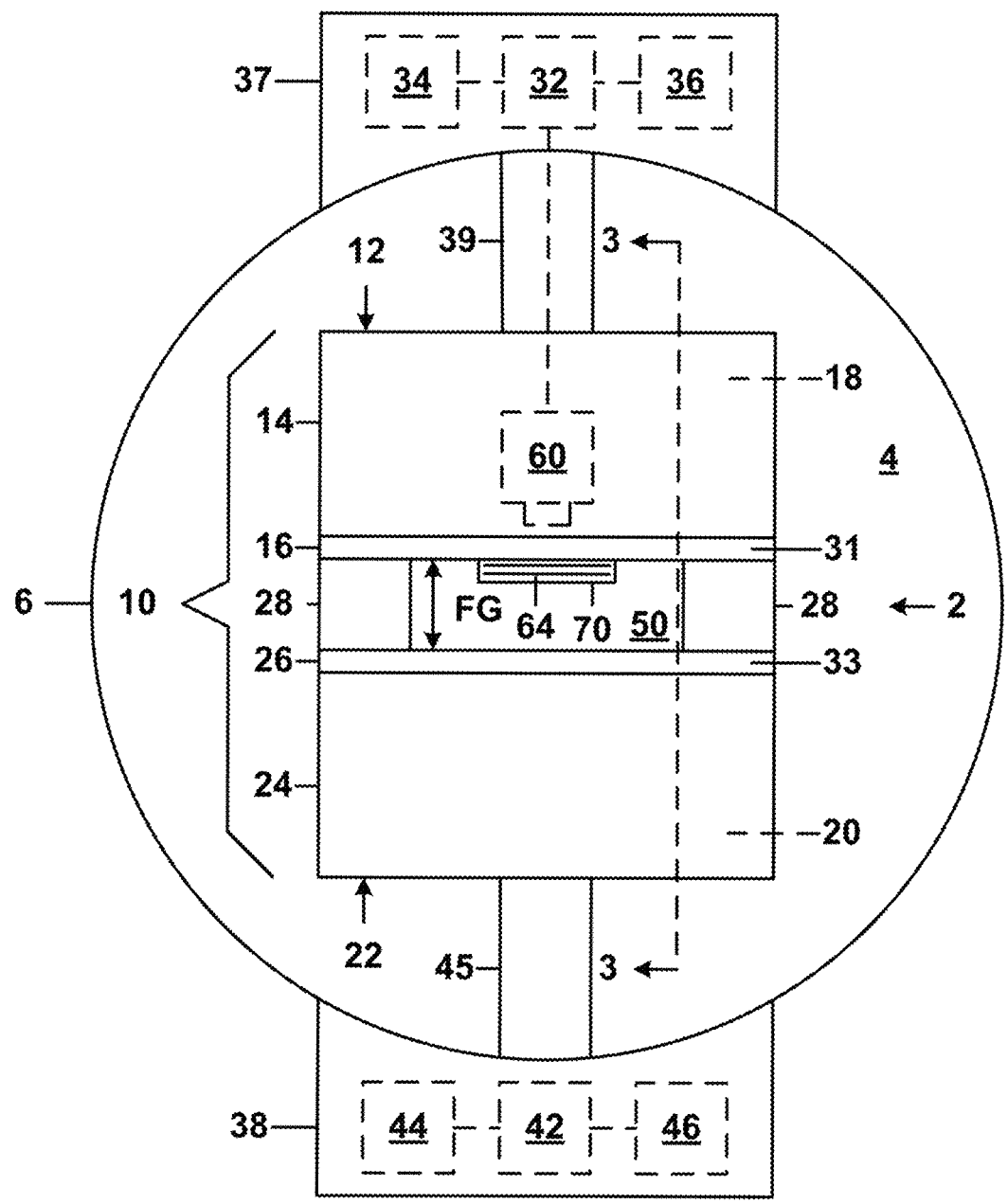
FIG. 1 is an inlet side end view of a sensor apparatus according to the present disclosure located in a pipeline.

It may be appreciated that the present disclosure is not limited in its application to the details of construction and the arrangement of components set forth in the following description or illustrated in the drawings. The embodiments herein may be capable of other embodiments and of being practiced or of being carried out in various ways. Also, it may be appreciated that the phraseology and terminology used herein is for the purpose of description and should not be regarded as limiting.

Referring now to the FIGS. 1-4, there is shown a sensor apparatus 2 according to a first embodiment of the present disclosure. As shown, sensor apparatus 2 is located within the flow passage 4 of pipeline 6. For the present embodiment, sensor apparatus 2 is shown fixed to the pipeline 6 as to remain stationary therewith during use therein. However, in other embodiments disclosed herein, the sensor apparatus 2 may be portable and mobile within the pipeline 6 during use therein. Among other fluids, pipeline 6 may be constructed and arranged to contain and transport a fluid mixture 8, such as a multi-phase fluid mixture of water and crude oil.

Sensor apparatus 2 comprises a housing 10 comprising a first sealed enclosure 12 and a second sealed enclosure 22, which are both sealed in a fluid tight manner against ingress of fluid mixture 8. Enclosures 12, 22 may have a size, for example, of about 4 inches in length by 3 inches in width and 2 inches in height. When assembled, first enclosure 12 and second enclosure 22 are spaced at a predetermined distance from one another, which distance may be referred to as the fluid gap FG, by spacers 28 which partially define a fluid passage 50 having an inlet 52 and an outlet 54 for the fluid mixture 8 to flow therebetween.

As shown, enclosures 12, 22 are rectangular, but may have any suitable shape. Enclosure 12 may particularly comprise a receptacle/container 14 having an internal recess/cavity 18 which is openable and closeable by removable close-out cover 16. Similarly, enclosure 22 may particularly comprise a receptacle/container 24 having an internal recess/cavity 20 which is openable and closeable by removable close-out cover 26.

Covers 16, 26 provide a transparent wall 31 and 33, respectively, particularly configured to allow light to pass through the material without being scattered. As such, covers 16, 26 are particularly formed of a transparent material, such as a transparent glass or plastic. For example, covers 16, 26 may be made of a transparent thermoplastic such as polycarbonate (PC) or polymethyl methacrylate (PMMA).

Receptacles/containers 14, 24 may be made out of any suitable material and do not necessarily need to be transparent. However, if receptacles/containers 14, 24 are made of a transparent material, the outer surfaces thereof should be covered with an opaque coating to avoid external light from entering the receptacles/containers 14, 24 as will be explained in greater detail below. In certain embodiments, receptacles/containers 14 and 24 may be made of metal such steel (e.g. stainless steel) or aluminum, or an opaque plastic material. While receptacles/containers 14 and 24 are show to be of a same size and shape, they do not need to be so limited.

Figure 2:
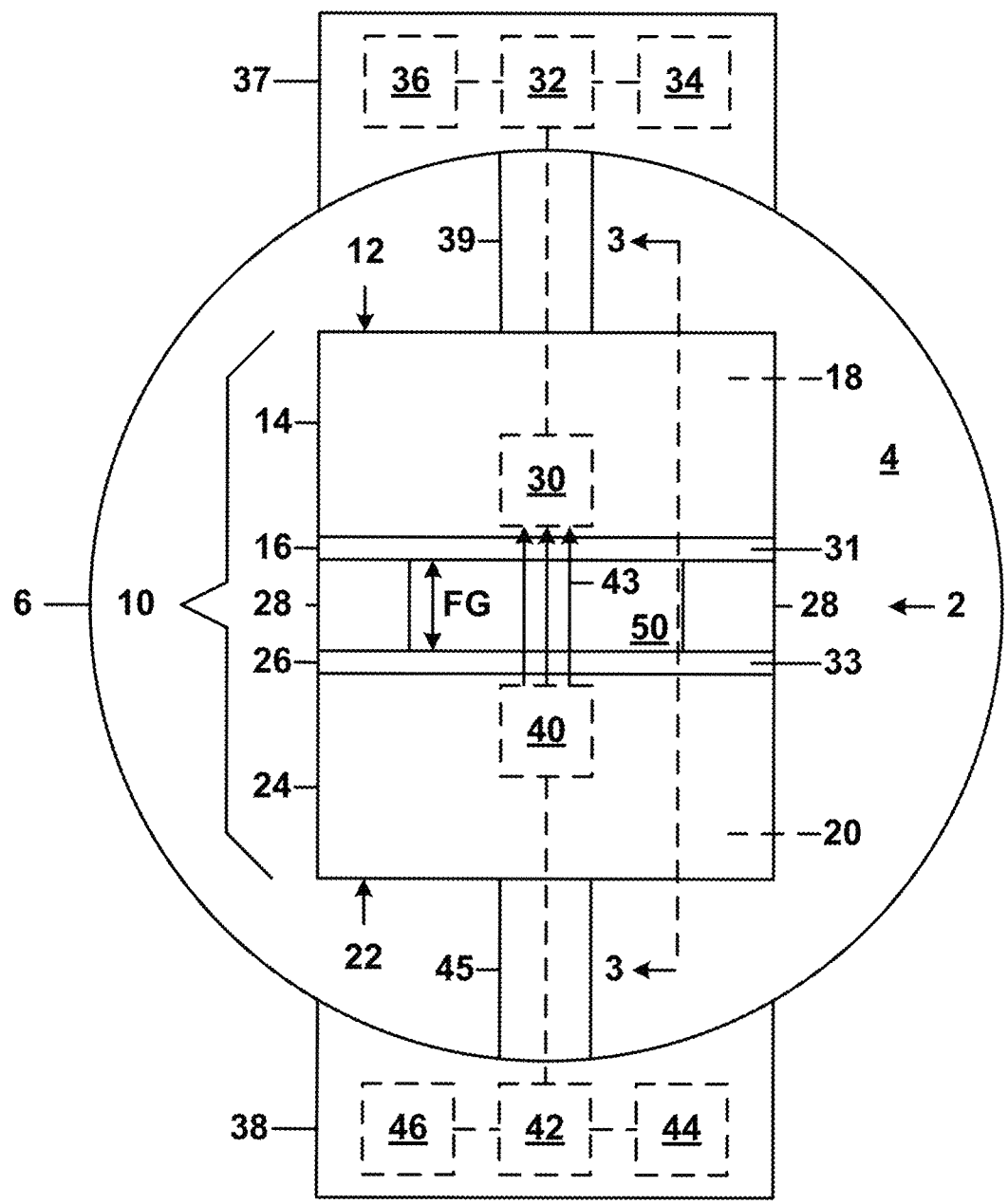
FIG. 2 is an outlet side end view of the sensor apparatus of FIG. 1.
Figure 3:
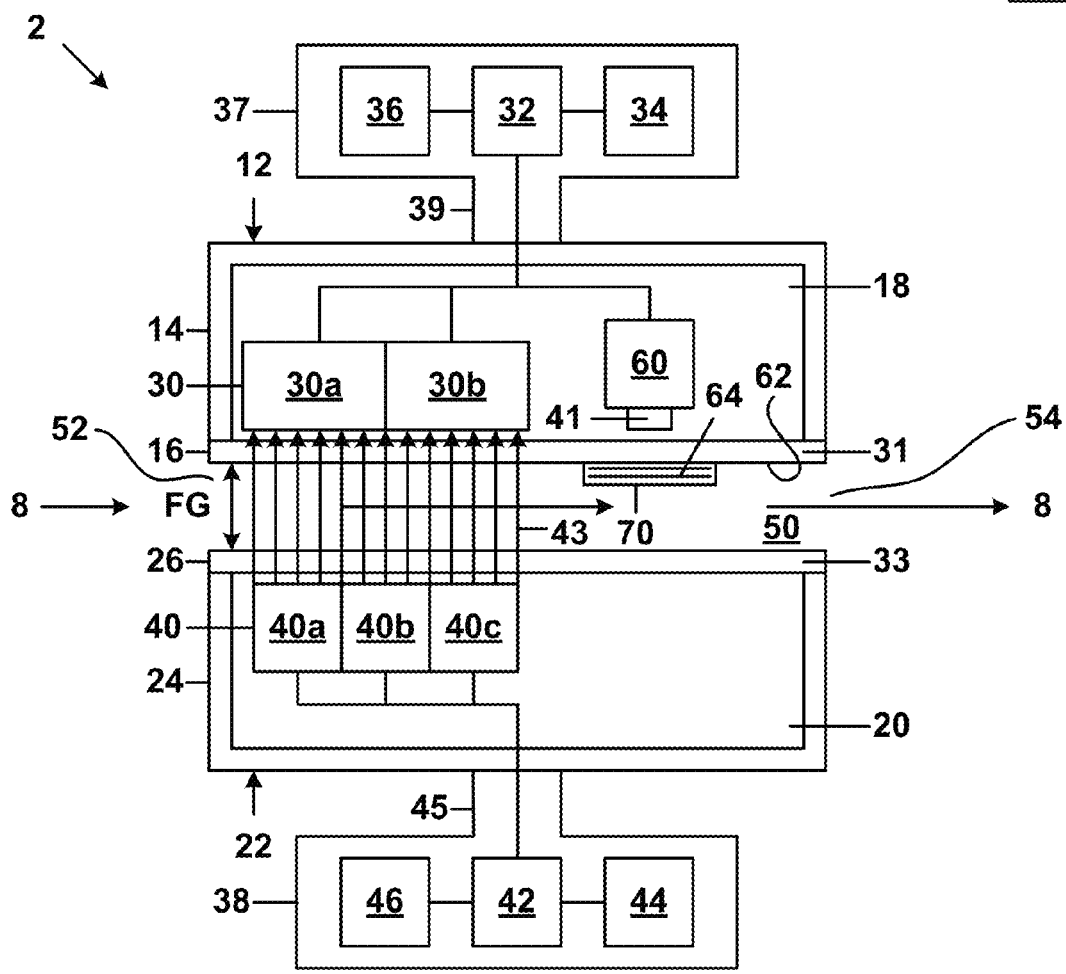
FIG. 3 is a longitudinal cross-sectional view of the sensor apparatus of FIG. 1 taken along section line 3-3 of FIG. 1.

As shown in FIG. 2, enclosure 12 contains at least one photodetector 30, which may be semiconductor photodetector such as a photodiode. As shown in FIG. 3, enclosure 12 may include a plurality of photodetectors 30a, 30b in the form of photodiodes. In certain embodiments, the photodiodes may have a dimension of 5.4 mm in length, by 4.3 mm in width and 3.2 mm in height, with a radiant sensitive area of 7.5 mm$^2$. The range of photodiode spectral bandwidth may be from 430 to 1,100 nm.

Enclosure 12 additionally includes an image recording device 60. Image recording device 60 may be a camera, such as a color camera. More particularly, the camera 60 may be a complementary metal-oxide-semiconductor (CMOS) color video camera. In certain embodiments, the image recording device 60, such as a CMOS camera, may have a 640×480 resolution (5.6 um×5.6 um unit pixel size) and a 70° lens angle.

Photodetectors 30a, 30b and image recording device 60 may be wired to a data acquisition system 32 which may include a computer microprocessor and a computer readable storage memory including one or more computer programs particularly for acquiring data and performing functions related to data acquisition and the operation of sensor apparatus 2 as a sensor. The data acquisition system 32, as well as the image recording device 60 may be powered by a suitable power source 34. Furthermore, the sensor apparatus 2 may include a transceiver 36 configured to provide wireless communication between the data acquisition system 32 of enclosure 12, such as provide real-time data of the senor apparatus 2 to a remote controller 35 which may be configured to operate the data acquisition system 32.

As shown, data acquisition system 32, power source 34 and transceiver 36 are all located outside pipeline 6 within a separate enclosure 37 which is connected to enclosure 12 by a conduit 39, through which communication wires/lines extend between the various components within enclosures 12, 37. In an alternative embodiment, data acquisition system 32, power source 34 and transceiver 36 may all be located within enclosure 12 and receptacle container 14 may be made magnetic as to provide temporary or permanent fixation to pipeline 6.

Figure 4:
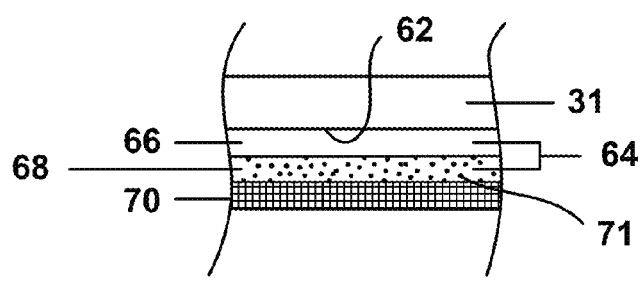
FIG. 4 is a close-up view of a portion of the sensor apparatus if FIG. 1.

As best shown in FIGS. 3 and 4, at least a portion of outer surface 62 of cover 16 is coated with a coating 64 which is color sensitive to pH level. Coating 64 may preferably include a first layer 66, which may comprise an oleophobic composition. An oleophobic composition herein may be understood as a coating that provides oil repelling characteristics. One preferred oleophobic coating is an oleophobic coating from Aculon identified as ON-305. The oleophobic coatings herein may provide a contact angle with crude oil (containing hydrocarbons of various molecular weights) of preferably about 55°, or in the range of 45°-75°.

Accordingly, an oleophobic coating composition applied to outer surface 62 is done to increase repellency to crude oil. A second layer 68 of the oleophobic composition may then be applied over the first layer 66 and include a pH indicator. However, in the broad context of the present disclosure, the pH indicator may be included in the first layer and the second layer may then be optional.

A protective overlying mesh 70 which is porous at least to the water phase, preferably made of a fluropolymer, such as polytetrafluoroethylene (PTFE), may be optionally applied over coating 64 to provide a barrier which may provide one or more of the following: (1) improvement to separation of the multiphase mixture; (2) increase in the residence (dwell) time of the water phase; and (3) reduction in the leach rate of the pH indicator from the oleophobic coating 64.

Enclosure 14 contains a light source 40 which may comprise a semiconductor light source such as at least one light emitting diode. As shown in FIG. 3, light source 40 may comprise a plurality of light emitting diodes 40a, 40b, 40c. Similar to the components of enclosure 12, light emitting diodes 40a, 40b, 40c of light source 40 may be wired to a data acquisition system 42 which may include a computer microprocessor and a computer readable storage memory including one or more computer programs particularly for acquiring data and performing functions related to data acquisition and the operation of sensor apparatus 2 as a sensor. The data acquisition system 42, as well as the light emitting diodes 40a, 40b, 40c may be powered by a suitable power source 44. Furthermore, the sensor apparatus 2 may include a transceiver 46 configured to provide wireless communication between the data acquisition system 42 of enclosure 22, such as to provide real-time data of the senor apparatus 2 to remote controller 35 which may be configured to operate the data acquisition system 42.

As shown, data acquisition system 42, power source 44 and transceiver 46 are all located outside pipeline 6 within a separate enclosure 38 which is connected to enclosure 22 by a conduit 45, through which communication wires/lines extend between the various components within enclosures 22, 38. In an alternative embodiment, data acquisition system 42, power source 44 and transceiver 46 may all be located within enclosure 22 and receptacle container 24 may be made magnetic as to provide temporary or permanent fixation to pipeline 6.

The light emitting diodes 40a, 40b, 40c may be arranged in a row and spaced approximately 3 mm apart from each other. In certain embodiments, the light emitting diodes 40a, 40b, 40c may comprise type T-1¾ (5 mm diameter) light emitting diodes. Furthermore, the light emitting diodes may emit the same type of light or different types of light. For example, light emitting diode 40a may be a RGB (red-green-blue) type light emitting diode, while light emitting diode 40b may be an infrared light emitting diode (wavelengths from 750 nm to 1 mm) and light emitting diode 40c may be a white light emitting diode. One preferred overall emission wavelength range for the diodes 40a, 40b and 40c may be from 466 nm (blue) to 850 nm (infrared). In use, the light emitting diodes 40a, 40b, 40c may exhibit a forward potential drop in a range from 1.4 to 3.2 V with a maximum current of 20 mA. Emission wavelength values may range from 466 nm (blue) to 850 nm (infrared).

After placing the electronic components in the internal recess/cavity 18, 20 of each enclosure 12, 14, respectively, the enclosures 18, 20 may be sealed in a fluid tight manner with transparent covers 16, 26. Thereafter, the external surfaces of each enclosure 12, 14, as well as the spacers 28 may be coated with a first layer 66 of coating 64, which as noted, may preferably comprise an oleophobic composition from Aculon, Inc. (type ON-305 nano scale nonstick coating). Before the application of the oleophobic composition, the sensor surfaces, such as surface 62, may be thoroughly cleaned with ethanol and allowed to dry. The oleophobic composition may then be applied by a dip coating method, by immersing the enclosures 18, 20 in a bath of the oleophobic composition, which may be a solution, for 5 minutes. After removal from the bath of the oleophobic composition, the oleophobic composition may be allowed to air dry for approximately 10 minutes to provide first (oleophobic) layer 66.

Thereafter, once layer 66 is dried, a second layer 68 may be applied over the first layer 66. In particular, a solution consisting of a mixture of the oleophobic composition with a pH indicator 71, such as bromocresol green, may be applied to layer 66 on surface 62 of enclosure 12 in an area of about 4 cm² in front of the lens 31 of the image recording device 60. The material of second layer 68 may be applied and dried in similar manner to first layer 66 to provide coating 64 having two layers. Once dry, additional quantities of the mixture of the oleophobic composition with a pH indicator may further be reapplied to build the thickness of layer 68.

Testing of the pH indicator was performed by first treating transparent acrylic panels (3 in.×3 in.) with a mixture of the oleophobic composition and the bromocresol green pH indicator. The pH indicator, in the form of a fine powder, was mixed with the oleophobic composition in a glass vial. Three mixtures were explored using different amounts of bromocresol green pH indicator (0.5 g, 1 g, and 1.5 g dissolved in 5 g of oleophobic coating). In all three trials, a yellowish solution with a suspension of pH indicator particles 71 was produced.

To confirm operation of the pH indicator in the oleophobic composition, pH tests were carried out by placing droplets of buffer solutions of pH 2, 4, 7, and 10 over the treated panel surface. Change in color of the coating pH indicator was recorded for each trial.

Bromocresol green pH indicator has a known color transition pH of 4.0-5.4. As such, for droplets of the buffer solutions with a pH<7 (i.e. pH less than 7), there was no color change of the bromocresol green pH indicator. Also, for droplets of the buffer solutions with a pH≥7 (i.e. pH greater than or equal to 7), the buffer solution droplets exhibited a color change from clear (no visible color) to blue, indicating that the pH was indeed greater than the upper transition pH of the pH indicator. To determine the effect of the oil on the pH detection, additional testing was conducted by placing droplets of a mixture of crude oil and buffer solutions of pH 4, 7, and 10 over the panel surface. Change in color of the coating was recorded for each trial.

For the mixture of crude oil with buffer solutions of pH 4, 7, and 10, there was once again a change in color of the coating pH indicator when the pH≥7 due to the reaction of the pH indicator. From these results, it appears that the presence of crude oil does not have a detrimental effect on the ability of the pH indicator to detect changes in pH of the water component.

The pH indicator may particularly be a halochromic chemical compound or substance. It should be understood that the disclosure is not so limited to bromocresol green pH indicator, or limited to use of a single indicator. In other words, another pH indicator may be used alone, or different combinations of pH indicators may be used together to provide a plurality of pH indicators. For example, the pH indicator(s) may include any one or any combination of gentian violet, leucomalachite green (first or second transition), thymol blue (first or second transition), methyl yellow, bromophenol blue, congo red, methyl orange, bromocresol green, methyl red, azolitrim, bromocresol purple, bromothymol blue, phenol red, neutral red, naphtholphthalein, cresol red, phenolphthalein, thymolphthalein or alizarine yellow R.

After first layer 66 and second layer 68 have formed coating composition 64, sensor surface 62 may be cleaned. Thereafter, a 4 cm² section of protective mesh 70 which is porous/permeable to the water phase, particularly made of polytetrafluoroethylene (PTFE) and having a thickness of 1 mm with 1.5 by 1.5 mm pores may be affixed to surface 62 of enclosure 12 in a manner overlying the portion of the surface 62 that includes first layer 66 of the oleophobic composition, and second layer 68 of the oleophobic composition with pH indicator. The porous protective mesh 70 is to provide a barrier which is relatively less permeable to the crude oil phase than the water phase, which may improve separation of the multiphase mixture, increase the residence time of the water phase in contact with the pH indicator, minimize convection of the water phase near surface 62 in front of the image recording device 60, and reduce the leach out rate of the pH indicator from layer 68.

Once coating composition 64 and protective mesh 66 are applied to enclosure 12, enclosures 12 and 14 may be joined with spacers 28. In various embodiments, spacers 28 may have a have a thickness ranging, for example, from 1.5 mm to 5 mm (e.g. 1.6 mm, 3.175 mm, 5 mm) to create a fluid flow passage 50 there between being defined by a transparent walls 31, 33 provided by transparent covers 16, 26 of enclosures 12, 22, respectively, and having an adjustable fluid gap FG. In other words, the thickness of the fluid gap FG is made adjustable by changing the thickness of spacers 28.

When assembled, a water content sensor is provided by light source 40 and at least one photodetector 30 being arranged such that light 43 from the light source 40 is passable through the multiphase mixture 8 within fluid flow passage 50, and detectable by the photodetector 30. The photodetector 30 then converts the detected light from the light source 40 to an electrical output (voltage) indicative of the water content of the multiphase mixture 8.

As shown, the light source 40 and the at least one photodetector 30 are each arranged outside the flow passage 50 behind opposing portions of a transparent walls 31, 33 provided by transparent covers 16, 26 of enclosures 12, 22, respectively. The light source 50 and the at least one photodetector 30 face each other from opposing sides of the flow passage 50 such that light 43 from the light source 40 is detectable by the photodetector 30.

More particularly, light emitting diodes 40a, 40b, 40c and photodiodes 30a and 30b, are arranged perpendicular and parallel with each other. As a result, the light source 40 and the at least one photodetector 30 are arranged such that the light 43 from the light source 40 is passable through a portion of the transparent wall 33 adjacent the light source 40 and then through the multiphase mixture 8 and thereafter passable from the multiphase mixture 8 through a portion of the transparent wall 33 adjacent the at least one photodetector 30.

When assembled a pH sensor is also provided comprising image recording device 60 and coating 64 comprising a composition including at least one pH indicator that exhibits a color change indicative of a pH level of the water phase when exposed thereto, with the image recording device 60 arranged to record the color change of the pH indicator. As shown, the image recording device 60 is arranged outside the flow passage 50 adjacent the transparent wall 31 provided by transparent cover 16, with the lens 41 arranged to record a color change in the pH indicator through the transparent wall 31. More particularly, the pH indicator is provided in layer 68 of coating 64 over surface 62 of the transparent wall 31 provided by transparent cover 16, which is inside the flow passage 50, and the recording device 60 is arranged to record the color change of the pH indicator through the transparent wall 31 provided by transparent cover 16 behind surface 62.

Before exposing the sensor apparatus 2 to multiphase mixtures of water and crude oil, the response of each optical device, i.e. photodetectors (photodiodes) 30 was tested in air and in 3.5% wt NaCl solution to determine a baseline condition for background response of the photodiodes and water detection capability. The outcome of this initial test was to screen the optimum light source (LED) 40/photodetector (photodiode) 30 pair to measure water content in crude oil.

Figure 5:
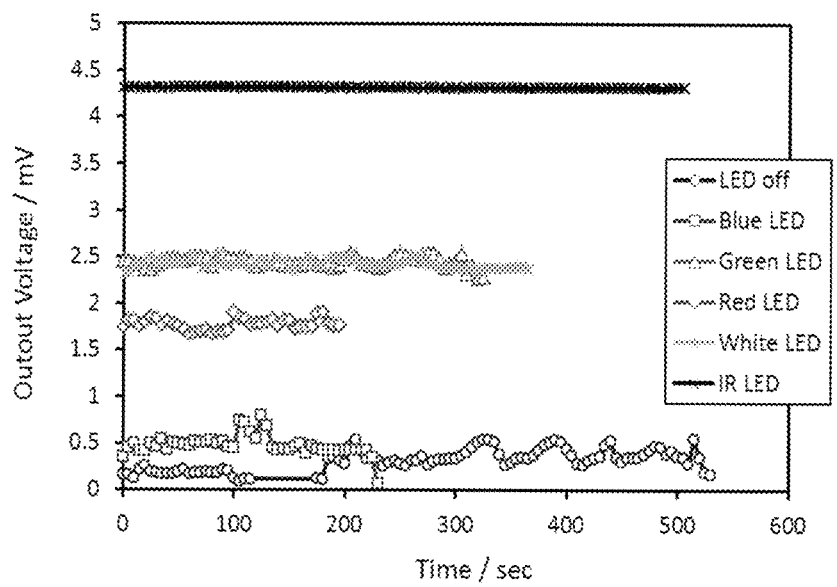
FIG. 5 is a graph of output voltage in air for the various LEDs/photodiode (average of the two photodiodes) of the sensor apparatus of FIG. 1.
Figure 6:
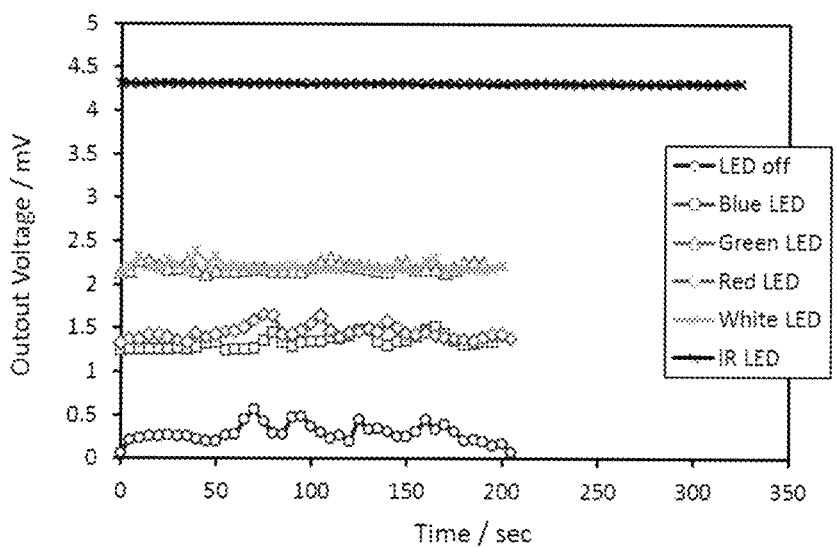
FIG. 6 is a graph of output voltage in 3.5% NaCl solution for the various LEDs/photodiode (average of the two photodiodes) of the sensor apparatus of FIG. 1
Figure 7A:
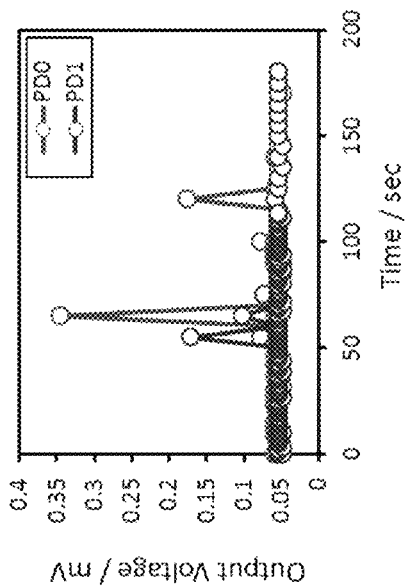
FIGS. 7A-7D are graphs of output voltage for the IR LED of the sensor apparatus in FIG. 1 in mixtures of oil/3.5% NaCl solution for a 1.6 mm fluid gap separation between the IR LED and photodiodes (labeled as PD0 and PD1) and a flow rate of 70 mL/min with the following water fractions WF: (A) WF=0, (B) WF=1%, (C) WF=5%, and (D) WF=10%.
Figure 7B:
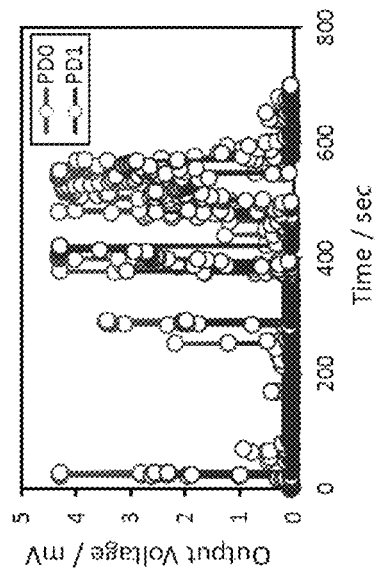
Figure 7C:
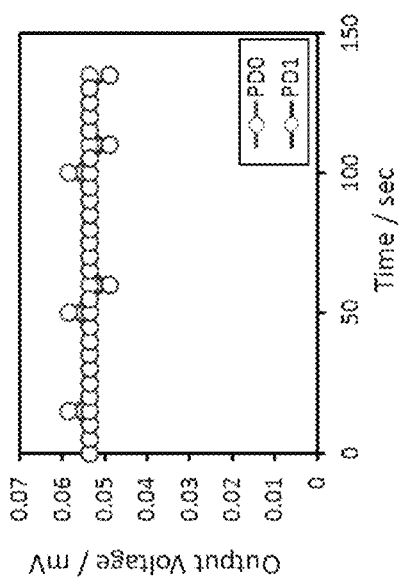
Figure 7D:
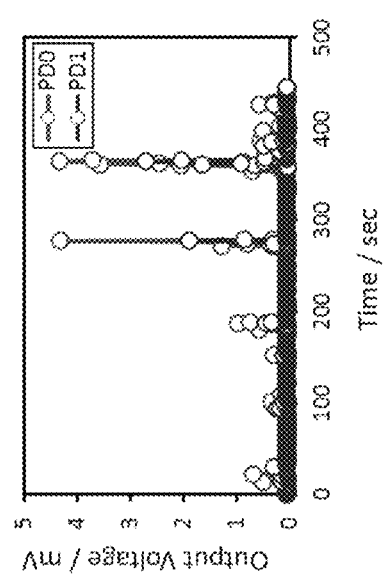
Figure 8B:
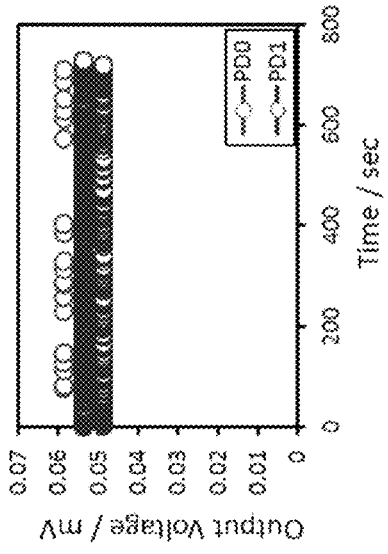
FIGS. 8A-8G are graphs of output voltage for the IR LED of the sensor apparatus in FIG. 1 in mixtures of oil/3.5% NaCl solution for a 5 mm fluid gap separation between the IR LED and photodiodes (labeled as PD0 and PD1) and a flow rate of 70 mL/min with the following water fractions WF: (A) WF=0, (B) WF=1%, (C) WF=5%, (D) WF=12%, (E) WF=16%, (F) WF=22%, and (G) WF=100%.
Figure 8D:
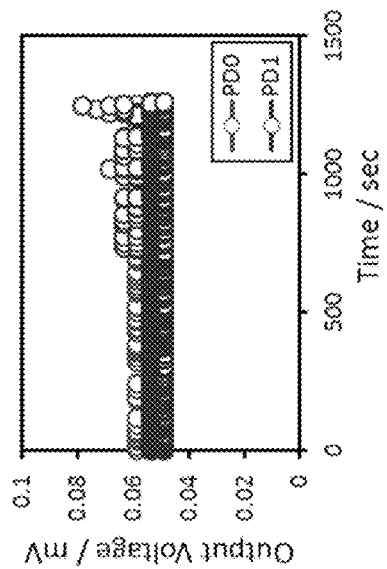
Figure 8A:
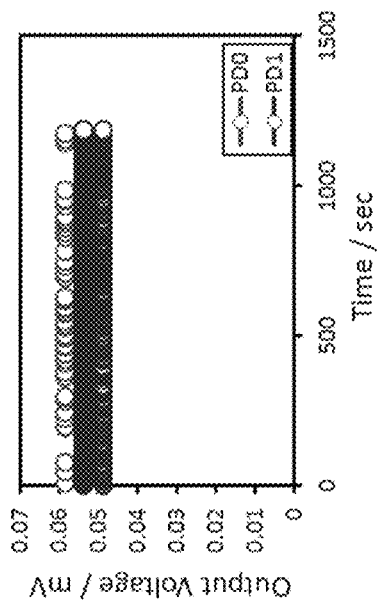
Figure 8C:
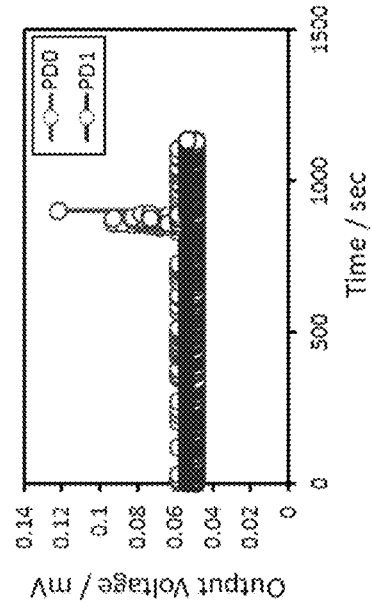
Figure 8F:
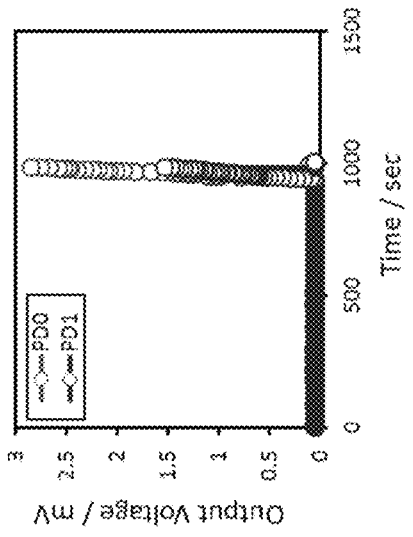
Figure 8E:
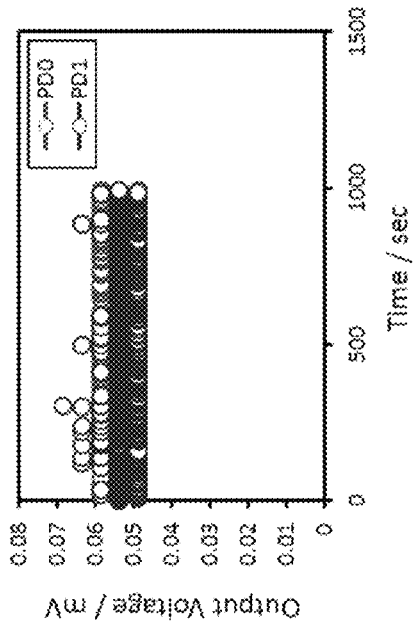
Figure 8G:
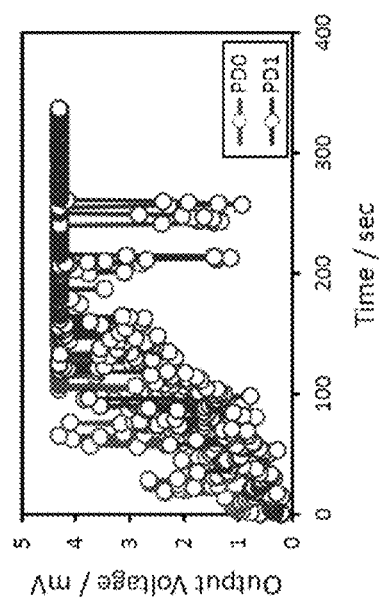

FIGS. 5 and 6 show the responses of the sensor apparatus 2 in air and in 3.5% wt NaCl solution, respectively. In air and with all the LEDs switched off, the photodiode output voltage varied from 0.09 to 0.55 mV with an average value of about 0.32 mV and a standard deviation of 0.12 mV. Comparable values were recorded in 3.5% wt NaCl solution, indicating that the photodiode detection is not affected by the presence of an ionic electrolyte. Next, the same tests were repeated using one LED type light source at a time.

The results showed distinctive behavior between the LEDs 40a, 40b, 40c tested of light source 40. For instance, the output voltage of the infrared LED 40b was the greatest (~4.3 mV) for both in air and in 3.5% wt NaCl solution and remained nearly constant throughout the test. The remaining LEDs 40a and 40c showed somewhat different trends in air and in 3.5% wt NaCl solution along with some degree of output voltage instability. Tables 1 and 2 summarize the output voltage readings for all the LEDs 40a, 40b, 40c examined in air and 3.5% wt NaCl solution.

TABLE 1

LED/photodiode output potentials (voltage) in air

| | Photodiode 1 Output Voltage (mV) | | | | Photodiode 2 Output Voltage (mV) | | | |
|---|---|---|---|---|---|---|---|---|
| LED | Avg. | Std. | Max | Min | Avg. | Std. | Max | Min |
| Blue | 0.281 | 0.112 | 0.615 | 0.068 | 0.670 | 0.121 | 0.981 | 0.073 |
| Green | 0.578 | 0.111 | 0.767 | 0.244 | 4.314 | 0.003 | 4.321 | 4.312 |
| Red | 0.356 | 0.075 | 0.557 | 0.229 | 3.189 | 0.054 | 3.305 | 3.105 |
| White | 4.323 | 0.003 | 4.326 | 4.316 | 0.511 | 0.088 | 0.688 | 0.317 |
| IR | 4.317 | 0.003 | 4.326 | 4.312 | 4.311 | 0.001 | 4.312 | 4.307 |

TABLE 2

LED/photodiode output potentials (voltage) in 3.5% NaCl

| | Photodiode 1 Output Voltage (mV) | | | | Photodiode 2 Output Voltage (mV) | | | |
|---|---|---|---|---|---|---|---|---|
| LED | Avg. | Std. | Max | Min | Avg. | Std. | Max | Min |
| Blue | 0.485 | 0.066 | 0.630 | 0.405 | 2.184 | 0.097 | 2.417 | 2.065 |
| Green | 0.584 | 0.045 | 0.674 | 0.508 | 3.812 | 0.052 | 3.921 | 3.726 |
| Red | 0.574 | 0.099 | 0.820 | 0.425 | 2.312 | 0.068 | 2.509 | 2.217 |
| White | 3.794 | 0.059 | 3.999 | 3.711 | 0.615 | 0.045 | 0.762 | 0.517 |
| IR | 4.313 | 0.003 | 4.316 | 4.307 | 4.311 | 0.002 | 4.312 | 4.307 |

From the foregoing results, it was concluded that the infrared LED 40b was best suited for free water measurement in crude oil. Indeed, a subsequent exploratory study carried out using a water/oil mixture with 20% water fraction demonstrated that all the LEDs, except for the infrared LED, were not sensitive to the presence of water in oil because the crude is opaque in the visual spectrum. Thus, infrared LED 40b was used for subsequent evaluations (preferred wavelength of 850 nm).

After initial testing, the sensor apparatus 2 was exposed to various multi-phase mixtures of oil and 3.5% wt sodium choride (NaCl) solution. Water fractions WF in the range of 0 to 100% were used. NaCl solution was sequentially added to the oil to attain the desired water fraction WF. Tests were conducted by placing the sensor apparatus 2 with the fluid flow channel 50 in a vertical orientation so that the test mixtures could easily flow between the fluid gap FG defined by the height of the flow passage 50 at flow rates of 70 mL/min and 100 mL/min. A high precision pump was used to recirculate the multi-phase mixture through the fluid gap FG/fluid flow passage 50. The oil/NaCl solution multi-phase mixture was agitated before pumping the mixture through the fluid gap FG/fluid flow passage 50.

In addition, testing was performed with spacers 28a, 28b having a thickness ranging of 1.6 mm, 3.175 mm and 5 mm. As should be understood, the thickness of the spacers 28a, 28b, determines the height of the fluid flow passage 50 and the corresponding fluid gap FG. The flow rate of the oil/NaCl solution was regulated so that the oil/NaCl solution multi-phase mixture filled the entire fluid gap FG/flow passage 50.

The tests were conducted at room temperature and atmospheric pressure. For each water fraction, tests were conducted for up to 400 sec and the sensor output potential (voltage) was recorded every 0.6 sec or 1 sec.

Figure 9E:
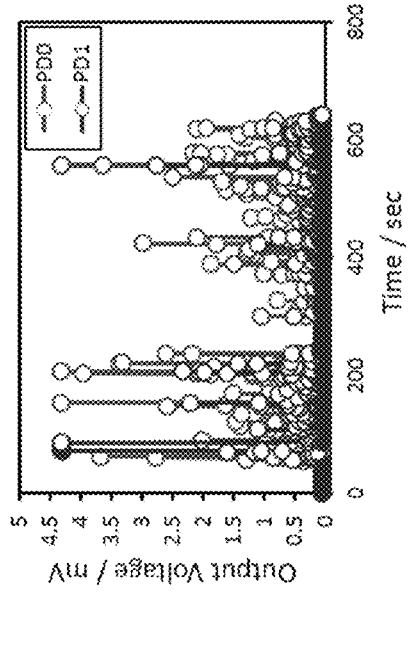
Figure 9F:
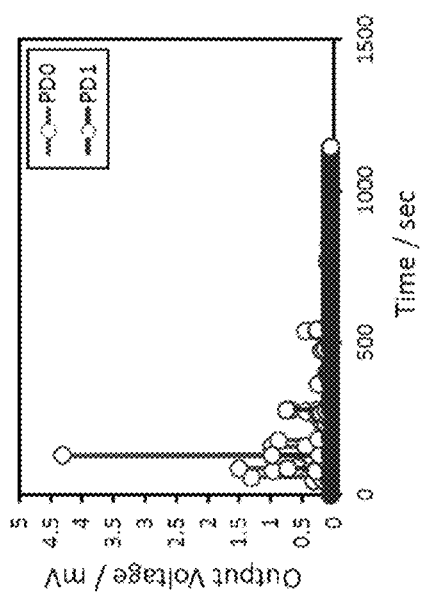
Figure 9G:
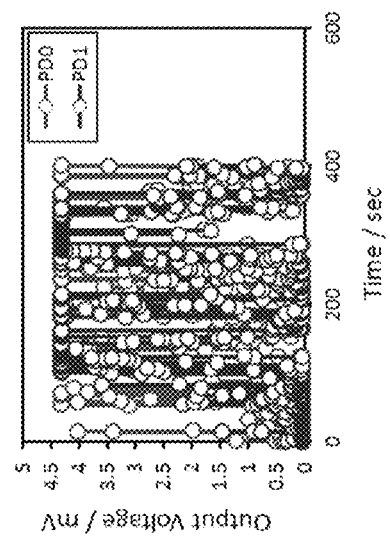

FIGS. 7 to 9 show responses of photodiodes 30*a*, 30*b* as a function of time, water fraction WF, LED/photodiode separation (fluid gap) and flow rate. FIGS. 7A to 7D display the photodiode response for water fractions ranging from 0 to 10% for a 1.6 mm height of the fluid gap FG/fluid flow passage 50, at a flow rate of 70 mL/min. More particularly, FIG. 7A has a WF of 0%; FIG. 7B has 1% WF; FIG. 7C has 5% WF and FIG. 7D has 10% WF. The plots show that for a water fraction WF=0, the photodiode response is the same as if no infrared source was present (i.e. same as photodiode background response). Similar trends were recorded for the photodiodes with increasing fluid gap FG exposed to a flow rate of 100 mL/min. See FIGS. 8A and 9A.

Figure 10:
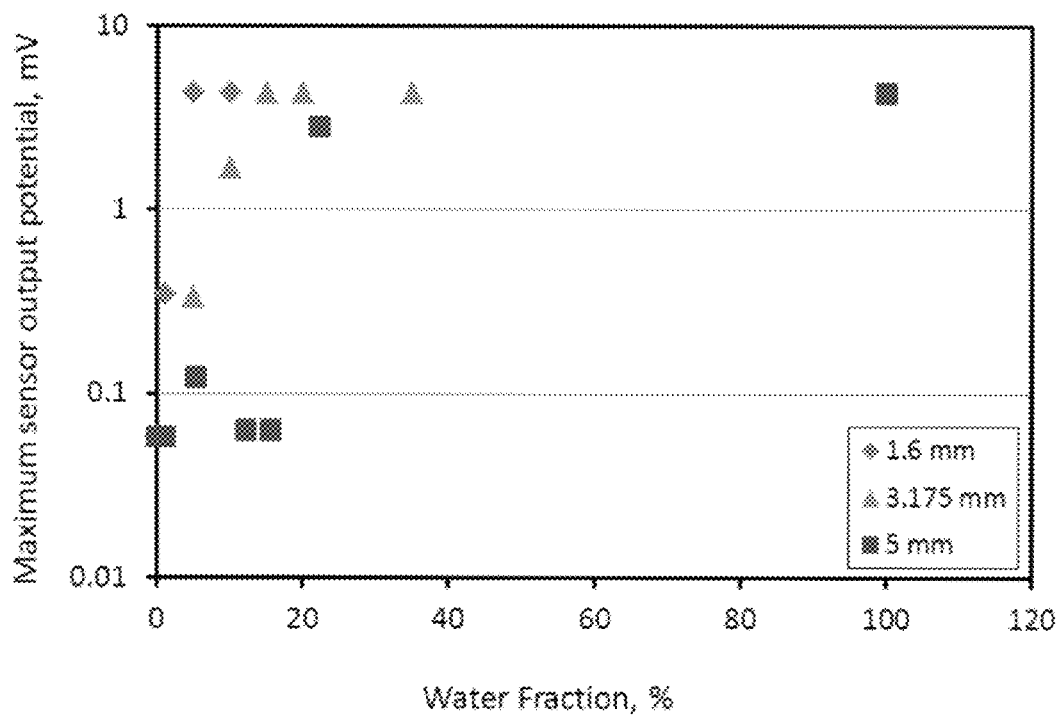
FIG. 10 is a chart showing maximum sensor output potential (voltage) as a function of water fraction WF for the different fluid gap separation between the IR LED and photodiodes of the sensor apparatus of FIG. 1.

As water fraction WF increased to 1% (FIG. 7B), there was a transient increase in the photodiode output potential (voltage). The output potential (voltage) magnitude and the frequency of the potential (voltage) spikes were directly proportional to the increase of the water fraction WF. See FIGS. 7C and 7D. As mentioned earlier, the presence of water in oil promoted a change in the overall infrared absorption as compared to the infrared absorption of pure oil (i.e. water fraction WF=0). Comparable trends were noted for the case of 3.175 mm fluid gap FG and a flow rate of 100 mL/min. This indicated that the photodiode response is not greatly affected by the solution flow rate for the range of flow rates examined. However, an increase in the fluid gap FG to 5 mm caused a decrease in photodiode sensitivity to water detection, especially at low water fraction WF (FIG. 10). Tables 3 to 5 summarize the photodiode response for each case explored.

TABLE 3

IR LED output potential (voltage) results for the case of 1.6 mm LED/photodiode separation and 70 mL/min flow rate

| | Photodiode 1 Output Voltage (mV) | | | | Photodiode 2 Output Voltage (mV) | | | |
|---|---|---|---|---|---|---|---|---|
| WF, % | Max | Min | Avg. | Std. | Max | Min | Avg. | Std. |
| 0 | 0.059 | 0.002 | 0.054 | 0.054 | 0.054 | 0.002 | 0.053 | 0.049 |
| 1 | 0.347 | 0.027 | 0.058 | 0.049 | 0.171 | 0.011 | 0.054 | 0.048 |
| 5 | 4.316 | 0.433 | 0.133 | 0.049 | 2.705 | 0.218 | 0.090 | 0.049 |
| 10 | 4.321 | 1.410 | 0.758 | 0.054 | 4.311 | 0.911 | 0.483 | 0.048 |

TABLE 4

IR LED output potential (voltage) results for the case of 3.175 mm LED/photodiode separation and 100 mL/min flow rate

| | Photodiode 1 Output Voltage (mV) | | | | Photodiode 2 Output Voltage (mV) | | | |
|---|---|---|---|---|---|---|---|---|
| WF, % | Max | Min | Avg. | Std. | Max | Min | Avg. | Std. |
| 0 | 0.059 | 0.049 | 0.055 | 0.002 | 0.054 | 0.049 | 0.053 | 0.002 |
| 1 | 0.059 | 0.049 | 0.054 | 0.002 | 0.063 | 0.049 | 0.053 | 0.002 |
| 5 | 0.337 | 0.049 | 0.055 | 0.009 | 0.054 | 0.049 | 0.053 | 0.002 |
| 10 | 1.685 | 0.049 | 0.058 | 0.058 | 0.415 | 0.049 | 0.054 | 0.020 |
| 15 | 4.321 | 0.049 | 0.062 | 0.116 | 0.977 | 0.049 | 0.055 | 0.036 |

TABLE 4-continued

IR LED output potential (voltage) results for the case of 3.175 mm LED/photodiode separation and 100 mL/min flow rate

| | Photodiode 1 Output Voltage (mV) | | | | Photodiode 2 Output Voltage (mV) | | | |
|---|---|---|---|---|---|---|---|---|
| WF, % | Max | Min | Avg. | Std. | Max | Min | Avg. | Std. |
| 20 | 4.321 | 0.049 | 0.337 | 0.771 | 4.312 | 0.049 | 0.221 | 0.661 |
| 35 | 4.321 | 0.049 | 2.117 | 1.910 | 4.312 | 0.049 | 1.774 | 1.770 |

TABLE 5

IR LED output potential (voltage) results for the case of 5 mm LED/photodiode separation and 70 mL/min flow rate

| | Photodiode 1 Output Voltage (mV) | | | | Photodiode 2 Output Voltage (mV) | | | |
|---|---|---|---|---|---|---|---|---|
| WF, % | Max | Min | Avg. | Std. | Max | Min | Avg. | Std. |
| 0 | 0.059 | 0.049 | 0.054 | 0.002 | 0.054 | 0.049 | 0.052 | 0.002 |
| 1 | 0.059 | 0.049 | 0.053 | 0.002 | 0.054 | 0.049 | 0.052 | 0.002 |
| 5 | 0.122 | 0.049 | 0.054 | 0.005 | 0.073 | 0.049 | 0.052 | 0.002 |
| 12 | 0.063 | 0.049 | 0.054 | 0.002 | 0.078 | 0.049 | 0.053 | 0.003 |
| 16 | 0.063 | 0.049 | 0.054 | 0.002 | 0.068 | 0.049 | 0.053 | 0.003 |
| 22 | 2.842 | 0.049 | 0.116 | 0.332 | 1.528 | 0.049 | 0.089 | 0.184 |
| 100 | 4.316 | 0.420 | 3.523 | 1.249 | 4.312 | 0.190 | 2.943 | 1.506 |

Figure 11:
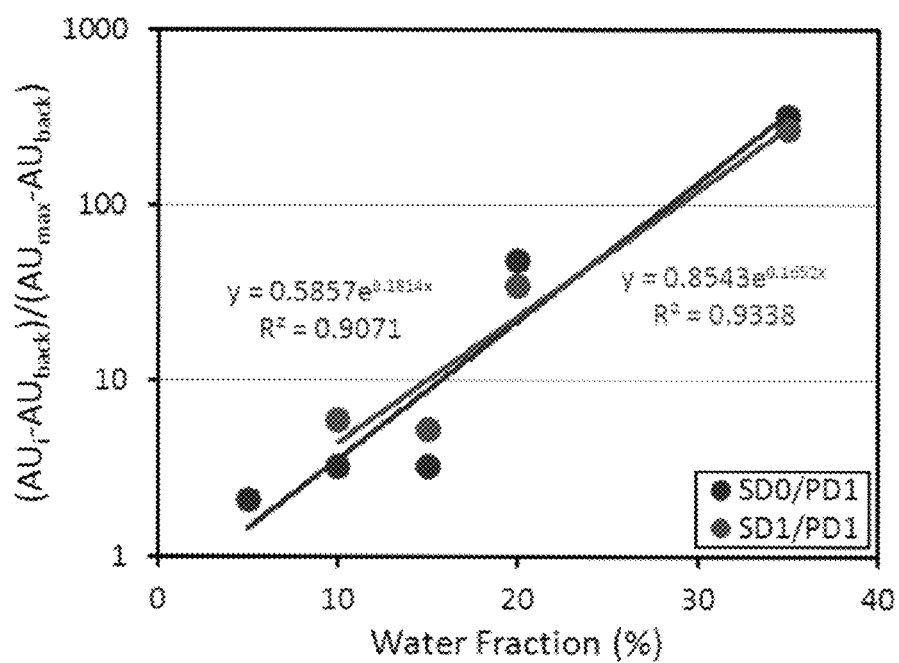
FIG. 11 shows calibration curves for the sensor apparatus of FIG. 1 obtained for the IR LED in mixtures of oil/3.5% NaCl solution for a 3.175 mm fluid gap separation between the IR LED and photodiodes (labeled as SD0/PD0 and SD1/PD1) and a flow rate of 100 mL/min.

For sensor calibration as a function of WF, the following equation was used:

$$\sum_i \frac{(AU_i - AU_{back})}{(AU_{max} - AU_{back})}$$

where $AU_i$ refers to the sensor output potential at a time interval i, $AU_{max}$ is the maximum sensor output potential, and $AU_{back}$ is the background sensor response for WF=0. Since the length of test time plays an important role in the probability of water detection, the above equation is applicable only if the test time is the same for all conditions. FIG. 11 shows an example of the sensor calibration curves obtained for the case of 3.175 mm LED/photodiode fluid gap FG and a flow rate of 100 mL/min for a total test time of 400 sec at each WF.

Concurrent to the determination of water content, pH measurements were monitored with the image recording device 60, a CMOS camera. This technique relies on the picture color change recorded by the camera particularly as the NaCL solution of the oil/NaCl solution mixture contacts the sensor surface 62 containing the pH-sensitive coating 68. Pictures were taken with the onboard camera 60 before, during, and after exposure to mixtures of oil and 3.5% wt NaCl solution.

Figure 12:
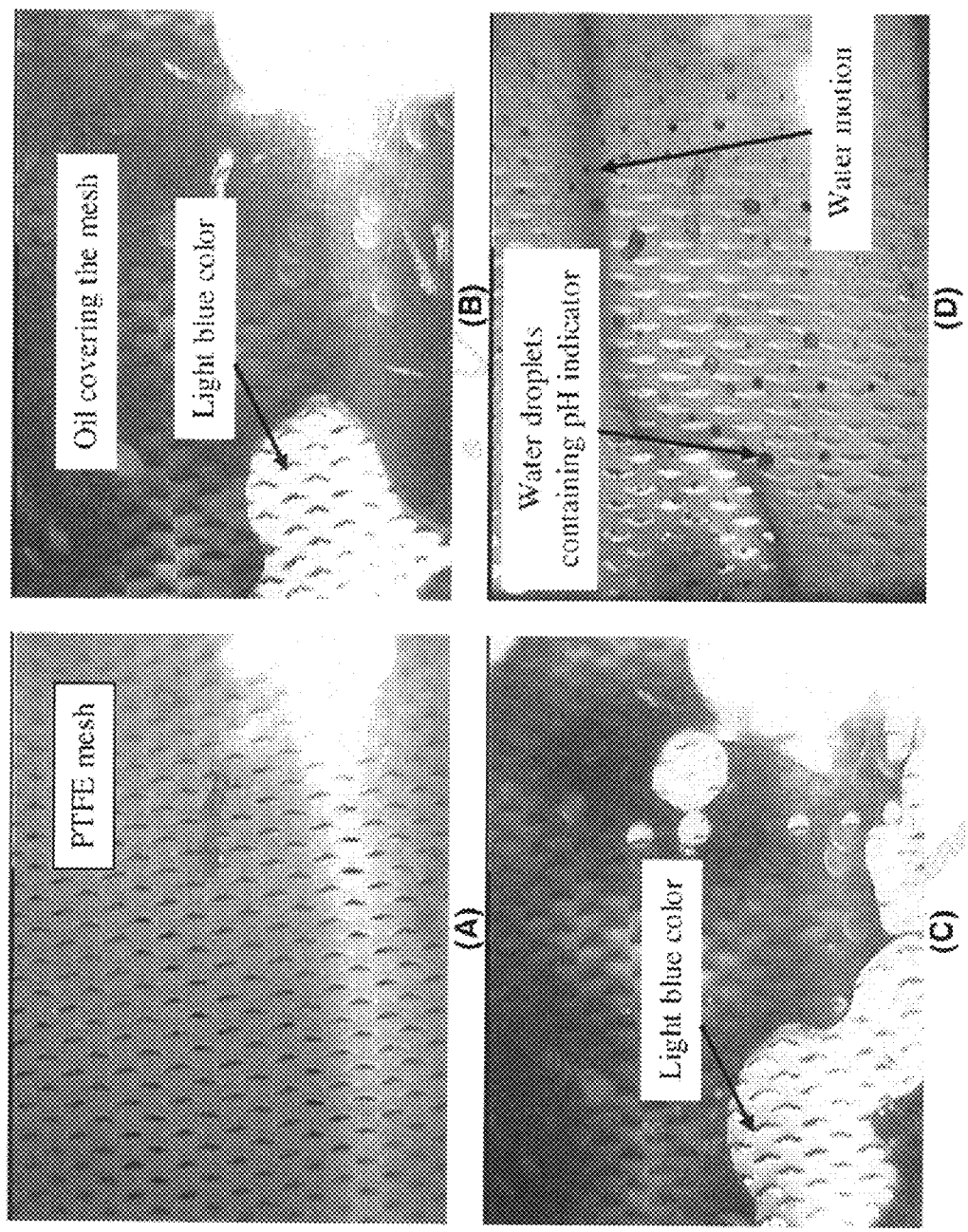
FIG. 12 shows the change in color of the pH sensitive coating when a crude oil/3.5% wt NaCl solution mixture with 20% WF (FIGS. 12B and 12C) and 100% WF (FIG. 12D) traveled through the fluid gap FG/fluid flow passage 50.

FIG. 12 shows a picture progression recorded by the image recording device 60, again a CMOS camera, in the sensor apparatus 2. FIG. 12A shows a typical picture of the coating 64 and overlying mesh 70 applied over surface 62, as viewed by the camera from behind transparent cover 16, prior to contact with crude oil/3.5% wt NaCl solution. FIGS. 12B and 12C show the appearance of the sensor surface as a function of time as the crude oil/3.5% wt NaCl solution mixture containing 20% water fraction WF traveled through the fluid gap FG/fluid flow passage 50. Light blue discoloration of the pH sensitive coating was noted, indicative of a solution pH greater than the indicator transition pH=5.4. FIG. 12D displays the sensor surface appearance when only water (100% WF) traveled through the fluid gap FG/fluid flow passage 50. Several droplets of blue-colored solution were noted on the sensor surface. Indeed, the 3.5% wt NaCl solution pH was about 6.5, so there was an agreement with the results obtained by the pH sensitive coating.

It should be understood that with ongoing use of sensor apparatus 2, the oleophobic coating 64, and in particular second layer 68, may wear upon exposure to the water and reduce in thickness. As layer 68 wears, it may be appreciated that particles of the pH indicator will continue to be exposed to the water from within the layer 68. In other words, particles of the pH indicator previously fully encapsulated in the layer 68 and previously not exposed to the water will now become unencapsulated as the layer 68 wears and exposed to the water, and thus provide continuous operation of the pH sensor until the layer 68 is completely worn and eliminated.

Figure 13:
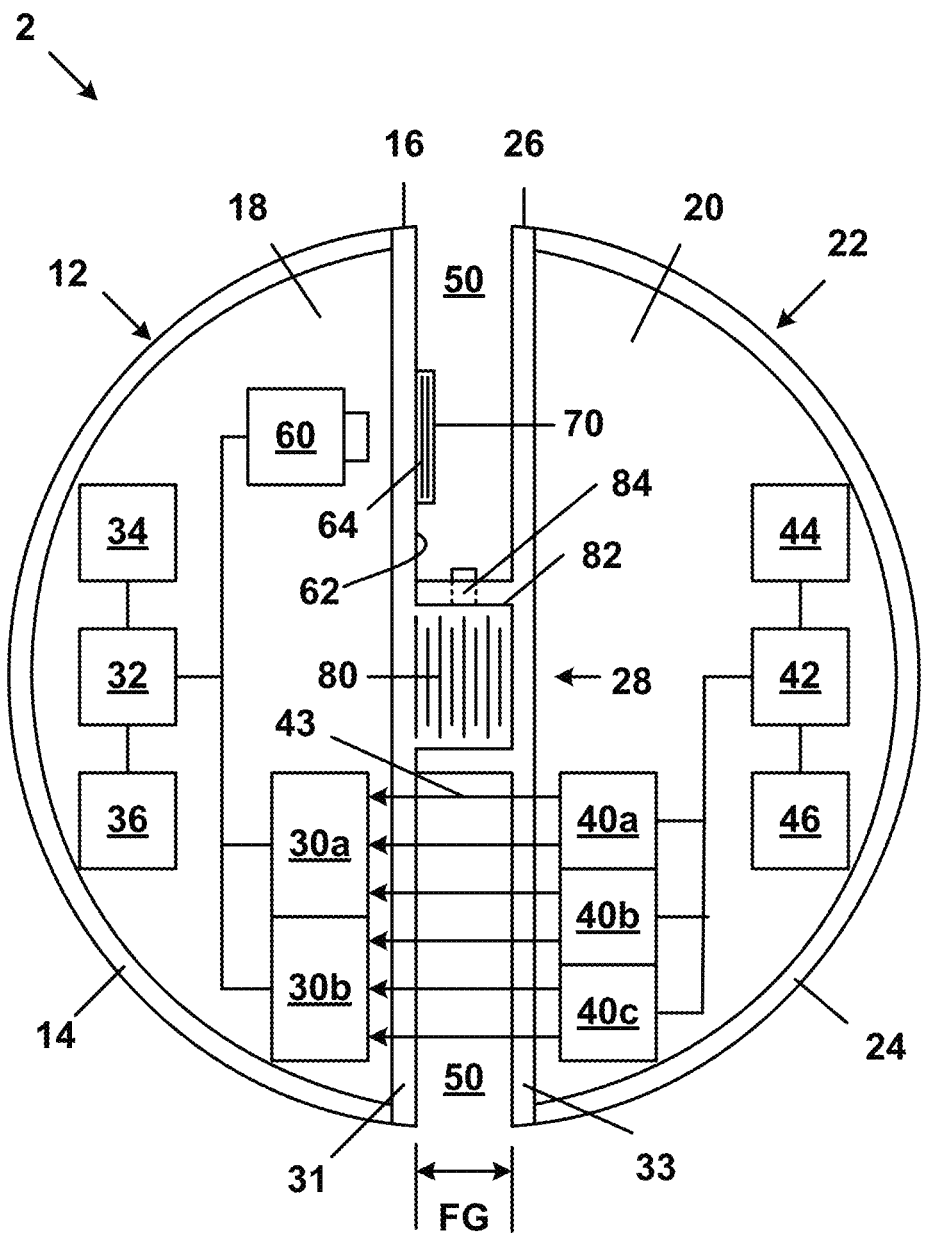
FIG. 13 is a cross-sectional view of another sensor apparatus according to the present invention.

In another embodiment of the sensor apparatus 2 shown in FIG. 13, sensor apparatus 2 may be spherical in shape as to be portable and mobile, particularly rollable, through pipeline 6 with the flow of fluid mixture 8 therein.

As shown, in FIG. 13 sensor apparatus 2 comprises enclosures 12, 22 which are hemi-spherical in shape, with spacer 28 located between the hemi-spherical enclosures 12, 22 forming s spindle. More particularly, spacer 28 comprises an externally threaded shank 80 which mates with threaded engagement with internally threaded blind bore 82. As such, the annular fluid gap FG between enclosures 12, 22 may be made quickly adjustable by rotating enclosures 12, 22 relative to one another in increments of 360 degrees (to ensure light emitting diodes 40a, 40b, 40c and photodiodes 30a and 30b remain in the same orientation relative to one another. Externally threaded shank 80 made be formed as part of close-out cover 16 and internally threaded blind bore 82 may be formed as part of close-out cover 26. Once the desired fluid gap FG between enclosures 12, 22 is achieved, the enclosures 12, 22 may be fixed relative to one another by locking set screw 84.

In addition to the foregoing, certain embodiments of sensor apparatus 2 may incorporate teachings of U.S. Publication No. 2008/0041173, the entirety of which is incorporated herein by reference.

Based on the foregoing disclosure, a sensor apparatus 2 is provided with an oleophobic coating 64 successfully impregnated with a pH indicator for in situ pH measurement of a water phase of a multi-phase oil/water fluid mixture when used in conjunction with an onboard image recording device 60, specifically a CMOS camera. The pH indicator can be tailored to monitor various pH regimes as needed. The onboard CMOS camera 60 in the sensor apparatus 2 was adequate to monitor changes in the water pH for various oil/water mixtures. In addition, the presence of the oleophobic coating did not have an adverse effect in the detection of water in oil.

Additionally, it has been demonstrated that the sensor apparatus 2 may be relatively sensitive to the presence of free water in crude oil. An increase in water detection sensitivity, especially for small water fractions WF, may be obtained by reducing the linear dimension of the flow passage, here the fluid gap FG, between the light source 40 and photodetector 30. However, a decrease in the dimensional distance between the light source 40 and photodetector 30 may decrease sensor sensitivity to water detection for larger water fractions WF. As such, it may be desirable to provide a sensor arrangement 2 with the ability to adjust the linear dimension of the flow passage between the light source (infrared LED) and photodetector (photodiode).

It has also been demonstrated that the combination of an infrared LED light source 40 with the photodiode photodetector 30 may provide the best detection of water fraction measurement in oil in the range of water fractions from 1 to 100%.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

What is claimed is:

1. An apparatus to measure water content and pH of a flowing multiphase fluid mixture of water and oil, the apparatus comprising:
    a first enclosure and a second enclosure spaced apart with a spacer to define a flow passage, wherein each of the enclosures are sealed and include a cavity;
    a first layer of an oleophobic coating applied to external surfaces of the first enclosure, the second enclosure and the spacer;
    the flow passage having an inlet and an outlet for the continuous passage of the flowing multiphase fluid mixture in through the inlet and out through the outlet of the flow passage;
    a water content sensor comprising an infrared light source arranged in said second enclosure and at least one photodetector arranged in said first enclosure on opposite sides of the flow passage such that light from the light source is passable through the second enclosure, through the flowing multiphase mixture in the flow passage, and through said first enclosure and is detectable by the photodetector, the photodetector arranged to convert the detected light from the light source to an electrical output indicative of the water content of the multiphase fluid mixture,
    a pH sensor comprising:
        a wearable oleophobic coating applied to at least a portion of said first layer of said oleophobic coating in said flow passage defined by said first enclosure, wherein said wearable oleophobic coating contains halochromic pH indicator particles that exhibit a color change indicative of a pH level of the water and said first layer of said oleophobic coating does not include said pH indicator particles, wherein a portion of said pH indicator particles are exposed to water and a portion of said pH particles are fully encapsulated by said wearable oleophobic coating, the wearable oleophobic coating being in direct contact with the flowing multiphase fluid mixture, and said wearable oleophobic coating provides continuous operation of said pH sensor,
        a porous, polytetrafluoroethylene mesh barrier overlying the wearable oleophobic coating and in direct contact with the flowing multiphase fluid mixture, wherein said porous mesh barrier is permeable to the water and is less permeable to the crude oil than the water, and
        an image recording device arranged in the first enclosure to record the color change of the pH indicator.

2. The apparatus of claim 1 wherein the flow passage for the multiphase mixture is a channel.

3. The apparatus of claim 1 wherein the apparatus is spherical and the flow passage is annular.

4. The apparatus of claim 1 wherein:
the flow passage is at least partially defined by a first transparent wall provided by a first cover removably affixed to the first enclosure and a second transparent wall provided by a second cover removably affixed to the second enclosure.

5. The apparatus of claim 4 wherein:
the light source and the at least one photodetector are arranged such that the light from the light source is passable through a portion of the second transparent wall adjacent the light source to the flowing multiphase mixture and thereafter passable from the multiphase mixture through a portion of the first transparent wall adjacent the at least one photodetector.

6. The apparatus of claim 4 wherein:
the image recording device is arranged outside the flow passage adjacent the first transparent wall.

7. The apparatus of claim 4 wherein:
the image recording device is arranged to record the color change of the pH indicator through the first transparent wall.

8. The apparatus of claim 4 wherein: the wearable oleophobic coating are disposed over a surface of the first transparent wall inside the flow passage; and
the recording device is arranged to record the color change of the pH indicator through the first transparent wall behind the surface.

9. The apparatus of claim 1 wherein the wearable oleophobic coating provides a contact angle with oil of 45° to 75°.

10. The apparatus of claim 4 wherein:
the wearable oleophobic coating are disposed over the first transparent wall inside the flow passage.

11. The apparatus of claim 1 wherein:
the halochromic pH indicator comprises a plurality of pH indicators.

12. The apparatus of claim 1 wherein:
the infrared light source comprises at least one light emitting diode.

13. The apparatus of claim 1 positioned in a pipeline.

* * * * *